United States Patent
Kito et al.

(10) Patent No.: US 12,414,700 B2
(45) Date of Patent: Sep. 16, 2025

(54) MONITORING DEVICE AND PHYSIOLOGICAL SIGNAL PROCESSING DEVICE

(71) Applicant: NIHON KOHDEN CORPORATION, Tokyo (JP)

(72) Inventors: Keito Kito, Tokorozawa (JP); Yoshiharu Harada, Tokorozawa (JP); Kenji Miyata, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 750 days.

(21) Appl. No.: 17/683,641

(22) Filed: Mar. 1, 2022

(65) Prior Publication Data

US 2022/0287581 A1    Sep. 15, 2022

(30) Foreign Application Priority Data

Mar. 10, 2021   (JP) .................................. 2021-038608

(51) Int. Cl.
*A61B 5/024* (2006.01)
*A61B 5/00* (2006.01)
*A61B 5/352* (2021.01)

(52) U.S. Cl.
CPC .......... *A61B 5/02433* (2013.01); *A61B 5/352* (2021.01); *A61B 5/7246* (2013.01)

(58) Field of Classification Search
CPC .............. A61B 5/02416; A61B 5/0205; A61B 5/02427; A61B 5/02433; A61B 5/0816;

(Continued)

(56) References Cited

U.S. PATENT DOCUMENTS

| 10,743,818 | B2 | 8/2020 | Brouse | |
|---|---|---|---|---|
| 2017/0290552 | A1 | 10/2017 | Naruse | |
| 2019/0298272 | A1* | 10/2019 | Persen | A61B 5/02405 |

FOREIGN PATENT DOCUMENTS

| JP | 2017-189288 A | 10/2017 |
|---|---|---|
| JP | 2019-122552 A | 7/2019 |
| JP | 2020-130875 A | 8/2020 |

OTHER PUBLICATIONS

Extended European Search Report dated Aug. 31, 2022, issued by the European Patent Office in counterpart European Patent Application No. 22159966.5.

(Continued)

*Primary Examiner* — Deborah L Malamud
(74) *Attorney, Agent, or Firm* — Sughrue Mion, PLLC

(57) ABSTRACT

A monitoring device includes a receiving unit, a processing unit, and an information providing unit. The receiving unit is configured to receive a first photoplethysmogram signal acquired by irradiating a body of a subject with a first light having a first wavelength, and a heartbeat signal corresponding to a heartbeat of the subject. The processing unit is configured to calculate a fundamental frequency of heart rate corresponding to a heart rate of the subject based on the heartbeat signal, and estimate a fundamental frequency of pulse rate of the subject by comparing the fundamental frequency of heart rate with a frequency component of the first photoplethysmogram signal. The information providing unit is configured to provide information acquired based on the fundamental frequency of pulse rate.

14 Claims, 4 Drawing Sheets

(58) Field of Classification Search
CPC ..... A61B 5/7264; A61B 5/1455; A61B 5/024;
A61B 5/7221; A61B 5/0059; A61B
5/02108; A61B 5/486; A61B 5/0261;
A61B 5/318; A61B 5/339; A61B 5/0295;
A61B 5/08; A61B 5/0004; A61B 5/00;
A61B 5/316; A61B 5/349; A61B 5/05;
A61B 5/0535; A61B 5/085; A61B 5/28;
A61B 5/24; A61B 5/72; A61B 5/74;
A61B 5/346; A61B 5/333
See application file for complete search history.

(56) References Cited

OTHER PUBLICATIONS

Office Action issued on Sep. 10, 2024 by the Japanese Patent Office in corresponding JP Patent Application No. 2021-038608.

* cited by examiner

MONITORING DEVICE AND PHYSIOLOGICAL SIGNAL PROCESSING DEVICE

CROSS-REFERENCE TO RELATED APPLICATIONS

This application is based on and claims priority under 35 USC 119 from Japanese Patent Application No. 2021-038608 filed on Mar. 10, 2021, the contents of which are incorporated herein by reference.

TECHNICAL FIELD

The presently disclosed subject matter relates to a monitoring device that provides information acquired based on a fundamental frequency of pulse rate of a subject. The presently disclosed subject matter also relates to a physiological signal processing device that processes photoplethysmogram signals and heartbeat signals to estimate the fundamental frequency of pulse rate, and a computer program executable by a processing unit of the physiological signal processing device.

BACKGROUND ART

Patent Literature 1 discloses a device that calculates a pulse rate of a subject based on a photoplethysmogram signal acquired from the subject. In calculating the pulse rate, a frequency component of the photoplethysmogram signal is analyzed with reference to a previously calculated pulse rate, so that a fundamental frequency of pulse rate is estimated.

CITATION LIST

Patent Literature

Patent Literature 1: JP2019-122552A

SUMMARY

An object of the presently disclosed subject matter is to prevent a decrease in estimation accuracy of a fundamental frequency of pulse rate due to body movement of a subject and the like.

A monitoring device according to a first aspect for achieving the above object may include:
- a receiving unit configured to receive a first photoplethysmogram signal acquired by irradiating a body of a subject with a first light having a first wavelength, and a heartbeat signal corresponding to a heartbeat of the subject;
- a processing unit configured to calculate a fundamental frequency of heart rate corresponding to a heart rate of the subject based on the heartbeat signal, and estimate a fundamental frequency of pulse rate of the subject by comparing the fundamental frequency of heart rate with a frequency component of the first photoplethysmogram signal; and
- an information providing unit configured to provide information acquired based on the fundamental frequency of pulse rate.

A physiological signal processing device according to a second aspect for achieving the above object may include:
- a receiving unit configured to receive a first photoplethysmogram signal acquired by irradiating a body of a subject with a first light having a first wavelength, and a heartbeat signal corresponding to a heartbeat of the subject; and
- a processing unit configured to calculate a fundamental frequency of heart rate corresponding to a heart rate of the subject based on the heartbeat signal, and estimate a fundamental frequency of pulse rate of the subject by comparing the fundamental frequency of heart rate with a frequency component of the first photoplethysmogram signal.

A computer program executable by a processing unit of a physiological signal processing device according to a third aspect for achieving the above object causes the physiological signal processing device to implement functions of:
- receiving a first photoplethysmogram signal acquired by irradiating a body of a subject with a first light having a first wavelength;
- receiving a heartbeat signal corresponding to a heartbeat of the subject,
- calculating a fundamental frequency of heart rate corresponding to a heart rate of the subject based on the heartbeat signal, and
- estimating a fundamental frequency of pulse rate of the subject by comparing the fundamental frequency of heart rate with a frequency component of the first photoplethysmogram signal.

When a noise component contained in the first photoplethysmogram signal is relatively small, the frequency component of the first photoplethysmogram signal has an obvious single peak frequency corresponding to a pulsating component. Therefore, this frequency can be regarded as the fundamental frequency of pulse rate of the subject. However, when a relatively large noise component is superimposed on the first photoplethysmogram signal due to body movement of the subject and the like, the frequency component of the first photoplethysmogram signal may include a plurality of peak frequencies. In this case, it becomes necessary to estimate the fundamental frequency of pulse rate with some method.

In the configuration according to each of the above aspects, based on an idea that a heartbeat and a pulse of a subject are likely to be correlated, the fundamental frequency of pulse rate is estimated based on comparison between the fundamental frequency of heart rate calculated based on the heartbeat signal and the frequency component in the first photoplethysmogram signal. As a result, it is possible to prevent a decrease in estimation accuracy of the fundamental frequency of pulse rate due to the body movement of the subject and the like.

DESCRIPTION OF EMBODIMENTS

Exemplary embodiments will be described in detail below with reference to the accompanying drawings. A scale of each drawing is appropriately changed so that each element to be described has a recognizable size.

Figure 1:
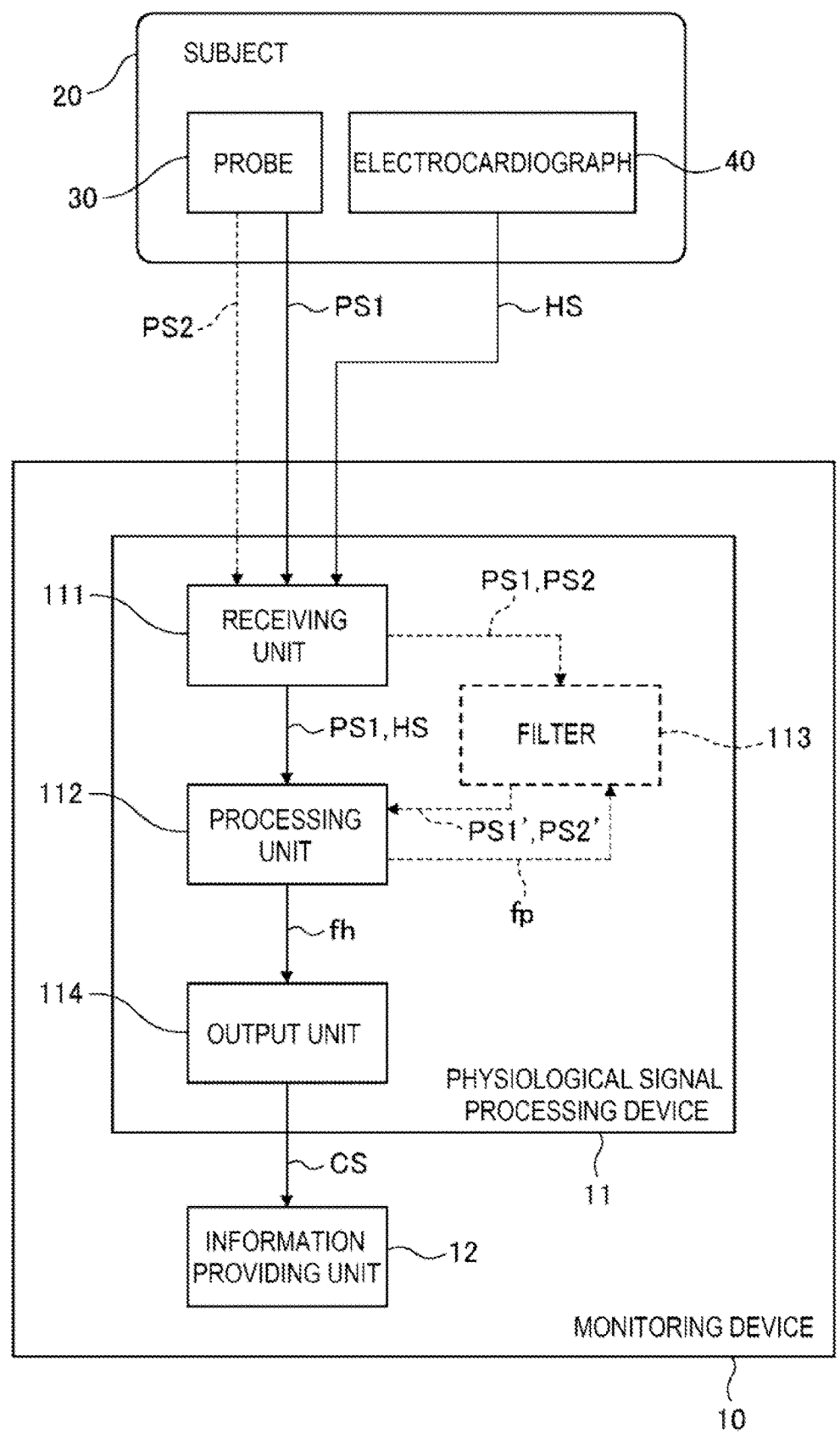
FIG. 1 illustrates a functional configuration of a monitoring device according to an embodiment.

FIG. 1 illustrates a functional configuration of a monitoring device 10 according to an embodiment. The monitoring device 10 is a device that provides a user with information acquired based on a fundamental frequency of pulse rate of a subject 20. The monitoring device 10 may include a physiological signal processing device 111 and an information providing unit 12.

The physiological signal processing device 11 is configured to estimate the fundamental frequency of pulse rate based on information related to a pulse rate and a heartbeat acquired from the subject 20. The physiological signal processing device 11 may include a receiving unit 11 and a processing unit 112.

The receiving unit 111 is configured as an interface that receives a first photoplethysmogram signal PS1 and a heartbeat signal HS. Each of the first photoplethysmogram signal PS1 and the heartbeat signal HS may be an analog signal or a digital signal. When each of the first photoplethysmogram signal PS1 and the heartbeat signal HS is an analog signal, the receiving unit 111 may include an appropriate conversion circuit including an A/D converter.

The first photoplethysmogram signal PS1 is acquired via a probe 30 attached to the subject 20. The probe 30 may include a light emitter and a light detector. The light emitter irradiates a body of the subject 20 with infrared light. The infrared light is an example of a first light. The infrared light transmitted through the body or reflected by the body is incident on the light detector. The light detector is sensitive to the infrared light and outputs the first photoplethysmogram signal PS1 having an amplitude corresponding to intensity of the infrared light incident on the light detector.

Since the infrared light is absorbed by blood flowing through blood vessels in the body, the intensity of the infrared light incident on the light detector is lower than intensity of the infrared light emitted from the light emitter. When the blood vessels pulsate with beating of a heart, an optical path length for the absorption changes, so that the intensity of the infrared light incident on the light detector also changes. That is, the amplitude of the first photoplethysmogram signal PS1 increases or decreases in response to the pulsation of the blood vessels. Since a ratio of the intensity of the infrared light emitted from the light emitter to the intensity of the infrared light incident on the light detector also changes, the amplitude of the first photoplethysmogram signal PS1 may also correspond to the ratio.

The heartbeat signal HS is a signal that exhibits change over time in an amplitude corresponding to the heartbeat of the subject 20. In this example, the heartbeat signal HS corresponds to an electrocardiogram signal output from an electrocardiograph 40, which is connected to the body of the subject 20.

Processing performed by the processing unit 112 will be described with reference to FIGS. 2 to 4.

The processing unit 112 acquires the first photoplethysmogram signal PS1 over a predetermined period (STEP1). As described above, the first photoplethysmogram signal PS1 is acquired via the receiving unit 111. FIG. 3 illustrates the acquired first photoplethysmogram signal PS1 by a solid line.

Subsequently, the processing unit 112 executes frequency analysis on the acquired first photoplethysmogram signal PS1 (STEP2). FIG. 4 illustrates a result of the frequency analysis on the first photoplethysmogram signal PS1 in FIG. 3 in the form of a frequency spectrum.

Figure 3:
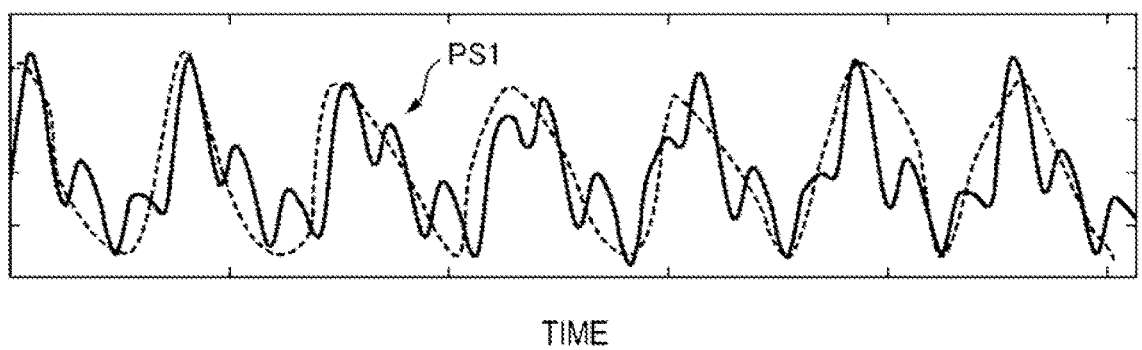
FIG. 3 is a diagram for explaining the processing executed by the processing unit in FIG. 1.

The acquired first photoplethysmogram signal PS1 is superposed with a respiratory noise component shown by a broken line in FIG. 3. Respiratory noise is generated due to body movement associated with breathing and change in blood volume in the blood vessels of the subject 20, and is superimposed on a pure pulsating component of the blood vessels. Since a fundamental frequency of the respiratory noise component is different from a fundamental frequency of the pulsating component, the frequency spectrum illustrated in FIG. 4 shows a peak frequency f1 reflecting the respiratory noise component and a peak frequency f2 reflecting the pulsating component.

Figure 2:
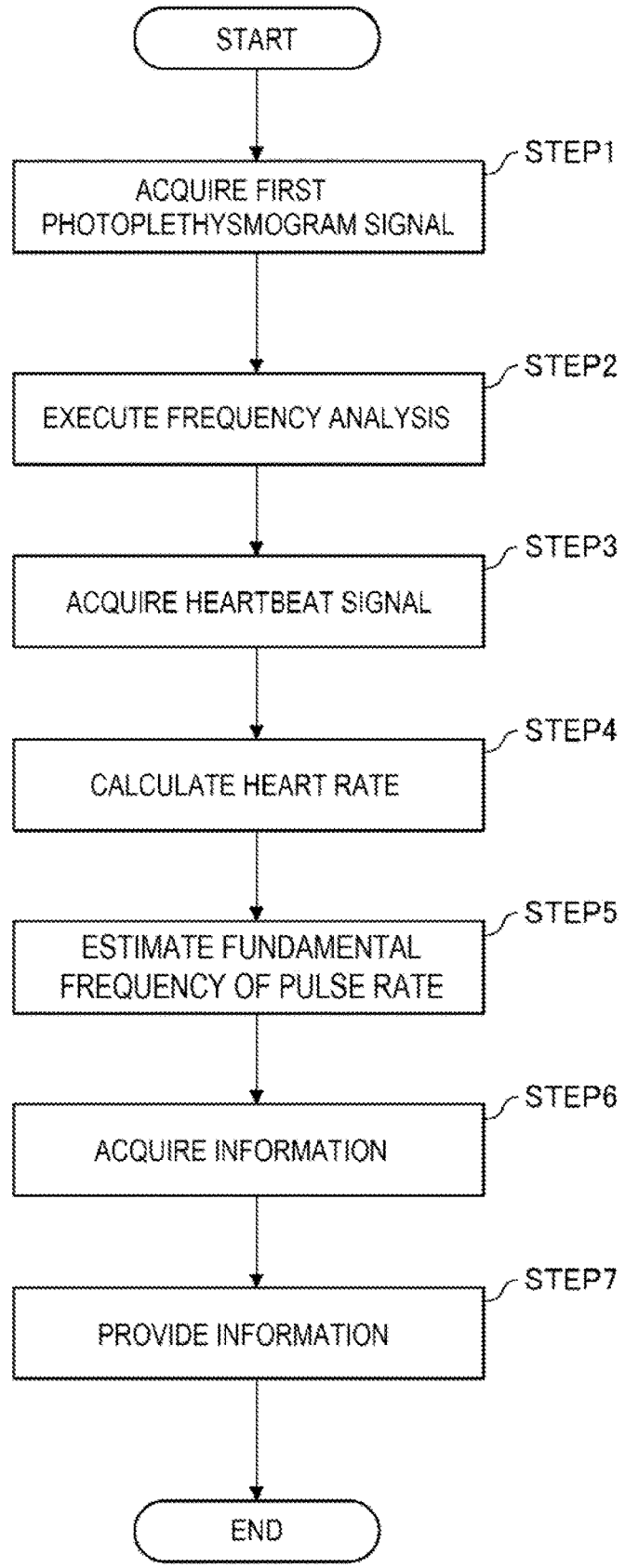
FIG. 2 illustrates a flow of processing executed by a processing unit in FIG. 1.

As illustrated in FIG. 2, the processing unit 112 acquires the heartbeat signal HS at the same timing as the first photoplethysmogram signal PS1 (STEP3). As described above, the heartbeat signal HS is acquired via the receiving unit 111.

Subsequently, the processing unit 112 calculates a fundamental frequency of heart rate fh corresponding to a heart rate of the subject 20 based on the acquired heartbeat signal HS (STEP4). The fundamental frequency of heart rate fh is calculated from an electrocardiogram waveform by a well-known method.

In FIG. 2, at least a part of processing of a first set including STEP1 and subsequent STEP2, and a part of processing of a second set including STEP3 and subsequent STEP4 may be performed in parallel. The processing of the second set may be started first and then the processing of the first set may be started.

Subsequently, the processing unit 112 estimates the fundamental frequency of pulse rate of the subject 20 (STEP5). Specifically, the processing unit 112 compares the fundamental frequency of heart rate fh calculated in STEP4 with the frequency component (frequency spectrum) of the first photoplethysmogram signal PS1 acquired in STEP2, to obtain a peak frequency closest to the fundamental frequency of heart rate fh as the fundamental frequency of pulse rate to be estimated.

Figure 4:
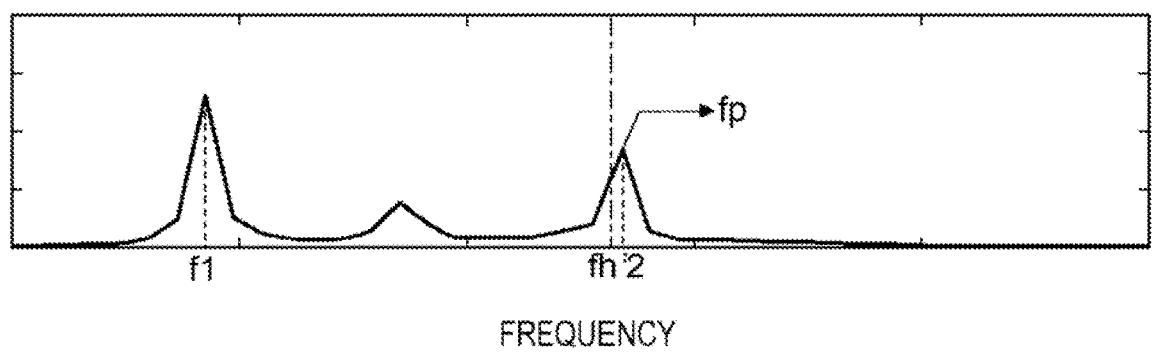
FIG. 4 is a diagram for explaining the processing executed by the processing unit in FIG. 1.

FIG. 4 illustrates the fundamental frequency of heart rate fh calculated in STEP4 superimposed on the frequency spectrum of the first photoplethysmogram signal PS1 acquired in STEP2. In this example, the peak frequency f2 is closest to the fundamental frequency of heart rate fh. Therefore, the peak frequency f2 is estimated to be the fundamental frequency of pulse rate fp of the subject 20.

When a noise component contained in the first photoplethysmogram signal PS1 is relatively small, the frequency component of the first photoplethysmogram signal PS1 has an obvious single peak frequency corresponding to the pulsating component. Therefore, this frequency can be regarded as the fundamental frequency of pulse rate of the subject 20. However, when a relatively large noise component due to the body movement of the subject 20 is superimposed on the first photoplethysmogram signal PS1, the frequency component of the first photoplethysmogram signal PS1 may include a plurality of peak frequencies. In this case, it becomes necessary to estimate the fundamental frequency of pulse rate with some method.

In the present embodiment, based on an idea that the heartbeat and the pulse of the subject 20 are likely to be correlated, the fundamental frequency of pulse rate is estimated based on comparison between the fundamental frequency of heart rate fh calculated based on the heartbeat signal HS and the frequency component in the first photoplethysmogram signal PS1. Accordingly, a decrease in estimation accuracy of the fundamental frequency of pulse rate due to the body movement of the subject 20 and the like can be prevented.

For example, when a process is applied to the frequency spectrum illustrated in FIG. 4 so that a peak frequency with the highest spectral intensity is estimated as the fundamental frequency of pulse rate, the fundamental frequency of pulse rate is wrongly estimated based on the peak frequency f1 corresponding to the respiratory noise component. In contrast, according to a method according to the present embodiment, the fundamental frequency of pulse rate can be estimated based on the peak frequency f2 corresponding to the pulsating component.

In addition to the condition of "a peak frequency closest to the fundamental frequency of heart rate fh", it is preferred to add a condition of "a peak frequency whose difference from the fundamental frequency of heart rate fh is less than a predetermined value" when estimating the fundamental frequency of pulse rate. According to this condition, it is possible to reduce a possibility that the estimation will be made based on a peak frequency corresponding to a noise component accidentally near the fundamental frequency of heart rate fh, in a situation where an obvious peak frequency corresponding to the pulsating component is not obtained.

In the present embodiment, the processing unit 112 uses an index of "RR interval" in the electrocardiogram signal to estimate the fundamental frequency of pulse rate. The "RR interval" represents an interval from a specific R wave to a next R wave appearing in the electrocardiogram signal.

Specifically, the processing unit 112 may be configured to calculate the fundamental frequency of heart rate fh when the electrocardiogram signal includes a predetermined number N or more of valid RR intervals within a predetermined time T. The predetermined time T is, for example, 8 seconds. The predetermined number N is, for example, 5.

Figure 5:
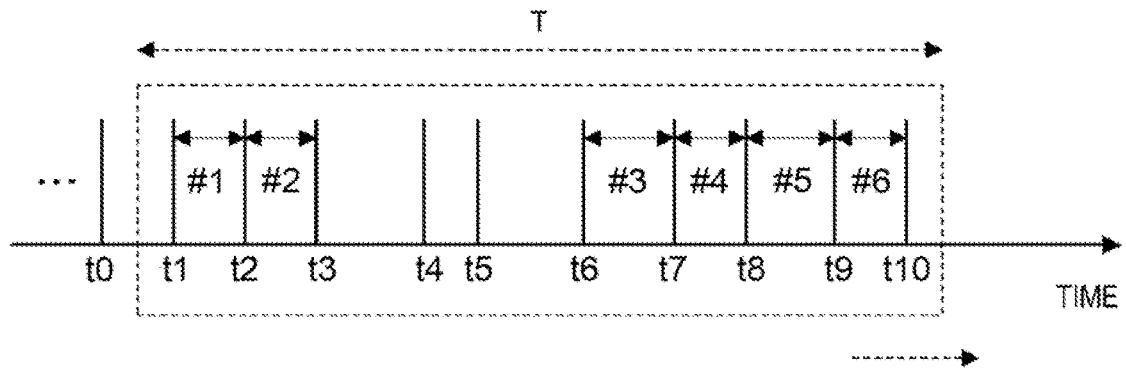
FIG. 5 is a diagram for explaining the processing executed by the processing unit in FIG. 1.

FIG. 5 illustrates an electrocardiogram signal obtained from a subject. A plurality of vertical bars arranged along a time axis schematically represent a QRS complex. In the drawing, numbers (#) are assigned to the RR intervals that are determined to be valid. The electrocardiogram signal in this example includes six valid RR intervals within the predetermined time T, so that the processing unit 112 calculates the fundamental frequency of heart rate fh based on the heartbeat signal HS corresponding to the electrocardiogram signal.

Specifically, a heart rate corresponding to an average value of N or more RR intervals determined to be valid is calculated, and the fundamental frequency of heart rate fh is calculated based on a reciprocal of the heart rate. It is preferable that the average value of the plurality of acquired RR intervals is acquired by averaging (N−2) or more RR intervals excluding a maximum value and a minimum value. In this case, influence due to noise can be further reduced.

Whether a specific RR interval is valid can be determined based on a plurality of conditions listed below. Specifically, if a specific RR interval satisfies all the plurality of conditions listed below, the RR interval is determined to be valid.

Condition 1: The RR interval is not associated with an arrhythmia.

Condition 2: The RR interval is included in a predetermined value range.

Condition 3: The RR interval has a fluctuation less than a predetermined value.

An algorithm for determining arrhythmia based on the RR interval is generally implemented in the electrocardiograph 40. Therefore, the heartbeat signal HS may include information relating to the arrhythmia imparted each time the RR interval is detected. The processing unit 112 can determine whether Condition 1 is satisfied by referring to the information.

The predetermined value range according to Condition 2 is defined as an RR interval corresponding to a value (such as 30 to 300) that a heart rate of a living body can take.

The "fluctuation" according to Condition 3 is obtained by calculating a ratio of an RR interval acquired at a certain time to an RR interval acquired immediately before that time. For example, the ratio may be calculated as a ratio of an RR interval acquired at a time t3 in FIG. 5 to an RR interval acquired at a time t2. The processing unit 122 determines whether a value of the ratio is less than a predetermined value.

In the example shown in FIG. 5, RR intervals acquired at times t4, t5, and t6 do not satisfy all of the above Conditions 1 to 3, and thus are determined by the processing unit 112 to be invalid.

According to such a configuration, information that does not contribute to appropriate calculation of the fundamental frequency of heart rate fh can be excluded, so that the decrease in estimation accuracy of the fundamental frequency of pulse rate due to noise can be prevented.

The processing unit 112 does not perform the above processing every time the predetermined time T elapses, but performs the above processing with a frame corresponding to the predetermined time T moves such that sections used for the processing overlap with each other. For example, in a case of the example illustrated in FIG. 5, after the above processing is performed for the predetermined time T including times t0 to t9, the above processing is performed for the predetermined time T including times t1 to t10. A movement amount of the frame (time period) can be appropriately set (for example, 1 second).

As illustrated in FIG. 2, the processing unit 112 acquires predetermined information relating to the subject 20 based on the estimated fundamental frequency of pulse rate (STEP6), and provides the information to the user of the monitoring device 10 (STEP7).

The pulse rate can be calculated as an example of the information relating to the subject 20. In this case, as illustrated in FIG. 1, the physiological signal processing device 11 may include a filter 113. The filter 113 is a digital filter that allows a signal in a specific frequency band to pass. In the following description, the specific frequency band referred to as a filter band is variable. The processing unit 112 sets the filter band of the filter 113 so as to include the fundamental frequency of pulse rate fp estimated by the above processing.

After setting the filter band, the processing unit 112 passes the first photoplethysmogram signal PS1 received by the receiving unit 111 through the filter 113. In a case of the example illustrated in FIG. 4, a band of the first photoplethysmogram signal PS1 near the peak frequency f2 passes through the filter 113, and a band near the peak frequency f1 is removed. As a result, as illustrated in FIG. 1, a first photoplethysmogram signal PS1' whose frequency components other than the pulsating component are reduced can be obtained.

The processing unit 112 calculates the pulse rate of the subject 20 based on the first photoplethysmogram signal PS1'. The calculation can be performed using a well-known method.

The physiological signal processing device 11 may include an output unit 114. The output unit 114 is configured as an interface that outputs a control signal CS that causes the information providing unit 12 to provide the pulse rate of the subject 20 calculated as described above. The control signal CS may be an analog signal or a digital signal. In a case where the control signal CS is an analog signal, the output unit 114 may include an appropriate conversion circuit including a D/A converter.

The information providing unit 12 receives the control signal CS and provides the calculated pulse rate to the user of the monitoring device 10 in a visual manner, an auditory manner, or a combination thereof. For example, the information providing unit 12 may include a screen. The calculated pulse rate can be displayed on the screen. The calculated pulse rate may also be visually provided as information by a light emitting apparatus that emits light in a color corresponding to the pulse rate. For example, the information providing unit 12 may include a speaker. The speaker can output a sound corresponding to the calculated pulse rate.

According to the above configuration, with the influence due to the body movement of the subject 20 and the like being reduced, calculation accuracy of the pulse rate can also be improved since the filter band of the filter 113 is set based on the estimated fundamental frequency of pulse rate fp, and the pulse rate of the subject 20 is calculated based on the first photoplethysmogram signal PS1' whose frequency components other than the pulsating component are reduced by the filter 113.

As another example of the information relating to the subject 20, a part corresponding to the pulse of the subject 20 in the first photoplethysmogram signal PS1 can be specified. Specifically, a peak waveform part that appears in a cycle corresponding to the fundamental frequency of pulse rate fp in the first photoplethysmogram signal PS1 is specified as the part corresponding to the pulse of the subject 20.

Figure 6:
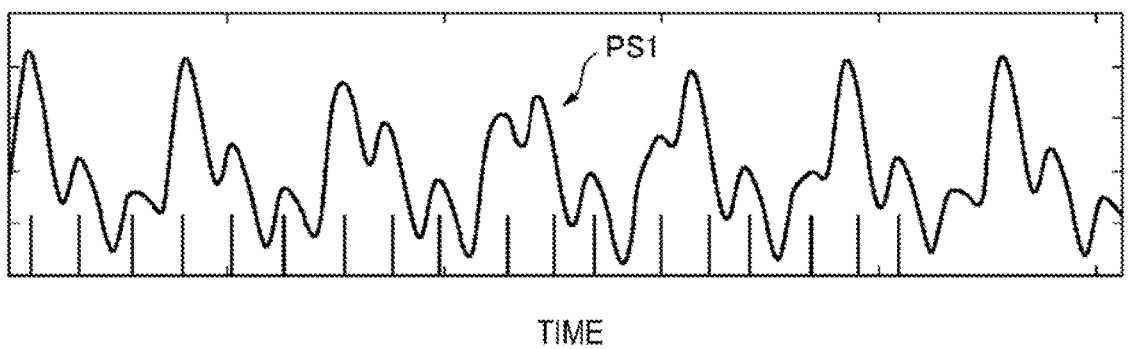
FIG. 6 is a diagram for explaining the processing executed by the processing unit in FIG. 1.

In this case, the output unit 114 outputs a control signal CS that causes the screen of the information providing unit 12 to display the first photoplethysmogram signal PS1 to which an annotation indicating the part corresponding to the pulse is added. In FIG. 6, the annotation is shown as a plurality of vertical bars below a waveform of the first photoplethysmogram signal PS1.

Such a configuration can help the user in specifying the part corresponding to the pulse of the subject 20 from the first photoplethysmogram signal PS1 on which the noise components are superimposed. Particularly, with the influence due to the body movement of the subject 20 being reduced, accuracy in specifying the part corresponding to the pulse can also be improved since the annotation is added based on the estimated fundamental frequency of pulse rate fp.

Whether the probe 30 is attached to the subject 20 can be determined as another example of the information relating to the subject 20.

Even in a case where the probe 30 is not properly attached to the body of the subject 20, the first photoplethysmogram signal PS1 whose amplitude increases and decreases periodically may still be output. The processing unit 112 compares the peak frequency appearing in the frequency spectrum of the first photoplethysmogram signal PS1 with the fundamental frequency of heart rate fh calculated based on the heartbeat signal HS. If there is no correlation between the two, it is highly probable that an increase or decrease in the amplitude of the first photoplethysmogram signal PS1 is caused not by pulsation but by the probe 30 not being properly attached to the body of the subject 20. Therefore, the processing unit 112 can determine whether the probe 30 is properly attached to the subject 20 based on the comparison result of the frequency component in the first photoplethysmogram signal PS1 with the fundamental frequency of heart rate fh.

The output unit 114 outputs a control signal CS that causes the information providing unit 12 to provide a determination result from the processing unit 112. For example, the information providing unit 12 that receives the control signal CS issues an alarm based on the determination result that the probe 30 is not properly attached, to the user of the monitoring device 10 in a visual manner, an auditory manner, or a combination thereof. For example, the alarm may be displayed on the screen of the information providing unit 12. The alarm may also be visually provided as information by a light emitting apparatus that emits light in a color corresponding to the alarm. In addition to or instead of the above, a sound corresponding to the alarm may be output through the speaker of the information providing unit 12.

According to the above configuration, with the influence due to the body movement of the subject 20 and the like being reduced, determination accuracy for encouraging the user to reattach the probe 30 can be improved since whether the probe 30 is properly attached is determined based on the estimated fundamental frequency of pulse rate fp.

A percutaneous arterial oxygen saturation (SpO2) can be calculated as another example of the information relating to the subject 20. SpO2 corresponds to a concentration of oxygenated hemoglobin in arterial blood of the subject 20. The oxygenated hemoglobin is an example of a blood light absorber. In this case, as illustrated in FIG. 1, the probe 30 is configured to output a second photoplethysmogram signal PS2. The second photoplethysmogram signal PS2 is also received by the receiving unit 111.

Specifically, the probe 30 may include a light emitter that emits red light and a light detector that is sensitive to red light. A light detector that is sensitive to both infrared light and red light may be shared. The red light is an example of a second light. A wavelength of infrared light and a wavelength of red light are appropriately selected as two wavelengths having different absorbance by the oxygenated hemoglobin. The wavelength of infrared light is an example of a first wavelength. The wavelength of red light is an example of a second wavelength. The light detector outputs the second photoplethysmogram signal PS2 having an amplitude corresponding to intensity of the red light incident on the light detector.

When the blood vessels pulsate with beating of the heart, an optical path length for the absorption of the red light changes, so that the intensity of the red light incident on the light detector also changes. That is, the amplitude of the second photoplethysmogram signal PS2 increases or decreases in response to the pulsation of the blood vessels. Since a ratio of intensity of the red light emitted from the light emitter to the intensity of the red light incident on the light detector also changes, the amplitude of the second photoplethysmogram signal PS2 may also correspond to the ratio.

The processing unit 112 sets the filter band of the filter 113 so as to include the estimated fundamental frequency of pulse rate fp, and then passes the second photoplethysmogram signal PS2 received by the receiving unit 11*l* through the filter 113. As a result, a second photoplethysmogram signal PS2' whose frequency components other than the pulsating component are reduced can be obtained.

The processing unit 112 calculates SpO2 of the subject 20 based on the first photoplethysmogram signal PS1' and the second photoplethysmogram signal PS2'. SpO2 is calculated by a well-known method based on a ratio of an amplitude of the first photoplethysmogram signal PS1' to an amplitude of the second photoplethysmogram signal PS2', which corresponds to a ratio of intensity of the red light and intensity of the infrared light received by the light detector.

The output unit 114 outputs a control signal CS that causes the information providing unit 12 to provide SpO2 of the subject 20 calculated as described above. The information providing unit 12 receives the control signal CS and provides the calculated SpO2 to the user of the monitoring device 10 in a visual manner, an auditory manner, or a combination thereof. For example, the information providing unit 12 may include a screen. The calculated SpO2 can be displayed on the screen. The calculated SpO2 may also be visually provided as information by a light emitting apparatus that emits light in a color corresponding to SpO2. For example, the information providing unit 12 may include a speaker. The speaker can output the calculated SpO2 or a sound corresponding to the calculated SpO2.

In calculating SpO2, light attenuation change of the red light and infrared light associated with the pulsation of the blood vessels may be taken into consideration. According to the above configuration, with the influence due to the body movement of the subject 20 and the like being reduced, calculation accuracy of SpO2 can also be improved since the filter band of the filter 113 is set based on the estimated fundamental frequency of pulse rate fp, and SpO2 of the subject 20 is calculated based on the first photoplethysmogram signal PS1' and the second photoplethysmogram signal PS2' whose frequency components other than the pulsating component are reduced by the filter 113.

Figure 7:
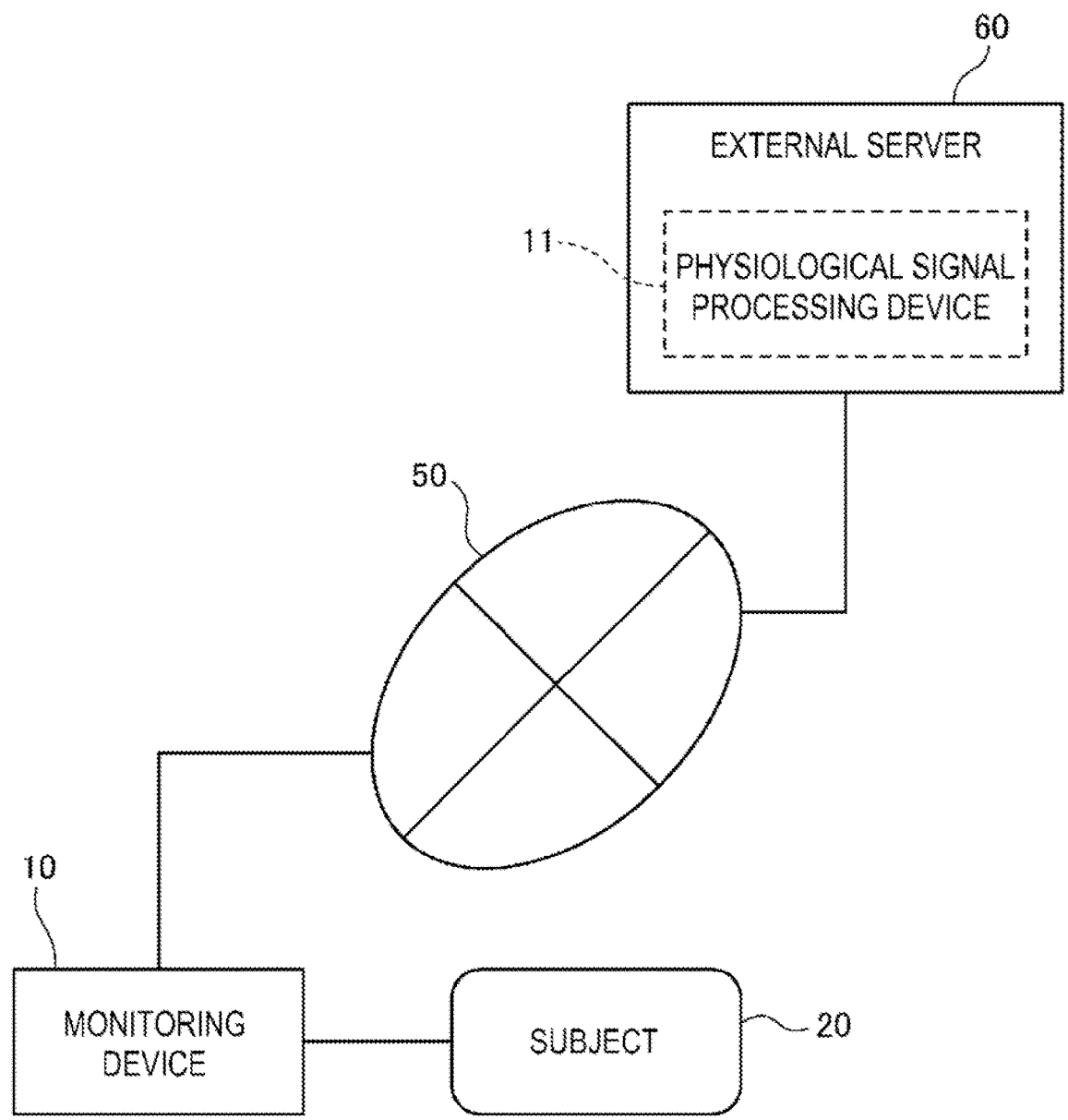
FIG. 7 illustrates another configuration example of the monitoring device and the physiological signal processing device in FIG. 1.

The processing unit 112 having various functions described above can be implemented by a general-purpose microprocessor that operates in cooperation with a general-purpose memory. Examples of the general-purpose microprocessor include CPUs, MPUs, and GPUs. Examples of the general-purpose memory include ROMs and RAMs. In this case, ROM may store a computer program that executes the above-described processing. ROM is an example of a non-transitory computer-readable medium in which the computer program is stored. The general-purpose microprocessor specifies at least a part of the computer program stored in ROM, deploys it on RAM, and implements the above-described processing in cooperation with RAM. The above-described computer program may be pre-installed in the general-purpose memory, or may be downloaded from an external server 60 via a communication network 50 illustrated in FIG. 7 and then installed in the general-purpose memory. In this case, the external server 60 is an example of the non-transitory computer-readable medium in which the computer program is stored.

The processing unit 112 having various functions described above may also be implemented by a dedicated integrated circuit capable of executing the above-mentioned computer program, such as microcontrollers, ASICs, and FPGAs. In this case, the above computer program is pre-installed in a storage device included in the dedicated integrated circuit. The storage device is an example of the non-transitory computer-readable medium in which the computer program is stored. The processing unit 112 can also be implemented by a combination of a general-purpose microprocessor and a dedicated integrated circuit.

The above embodiment is merely an example for facilitating understanding of the presently disclosed subject matter. The configurations according to the above embodiment can be appropriately changed or improved without departing from the gist of the presently disclosed subject matter.

In the above embodiment, the first photoplethysmogram signal PS1 generated by using the infrared light, which is known to be relatively resistant to the noise caused by the body movement, is processed by the physiological signal processing device 11. If necessary, the first photoplethysmogram signal PS1 generated by using the red light may also be processed.

In the above embodiment, SpO2 of the subject 20 is calculated using both the infrared light and the red light. However, at least two wavelengths used to calculate SpO2 may both be the infrared light or the red light as long as the two wavelengths have different values of blood extinction coefficient depending on oxygen saturation. Same or similarly, at least two wavelengths used to calculate a concentration of other blood light absorbers can be appropriately determined depending on absorption properties of the blood light absorbers. Examples of other blood light absorbers include not only substances produced in the body of the subject 20 such as carbon monoxide hemoglobin and methemoglobin, but also dyes injected into the blood vessels for contrast examination and the like.

In the above embodiment, the heartbeat signal HS is generated based on the electrocardiogram signal acquired via the electrocardiograph 40. This case is advantageous in that the information related to the arrhythmia can be included in the heartbeat signal HS as described above. The heart rate may be calculated by the electrocardiograph 40 based on the electrocardiogram signal, and the heartbeat signal HS corresponding to the heart rate may be generated. Instead of the electrocardiogram signal, the heartbeat signal HS may also be generated based on an invasive blood pressure signal obtained via a catheter. An amplitude of the invasive blood pressure signal also increases or decreases in response to the beating of the bean.

In the above embodiment, the physiological signal processing device 11 is mounted on the monitoring device 10. However, the physiological signal processing device 11 may be mounted on the external server 60 capable of communicating with the monitoring device 10 via the communication network 50 illustrated in FIG. 7. The communication between the monitoring device 10 and the external server device 60 may be wired communication or wireless communication. In this case, the monitoring device 10 may be configured to include a communication interface that transmits the first photoplethysmogram signal PS1, the second photoplethysmogram signal PS2, and the heartbeat signal HS to the external server 60, and receives the control signal CS from the external server 60.

The invention claimed is:
1. A monitoring device, comprising:
a receiving unit configured to receive a first photoplethysmogram signal acquired by irradiating a body of a subject with a first light having a first wavelength, and a heartbeat signal corresponding to a heartbeat of the subject;
a processing unit configured to calculate a fundamental frequency of heart rate corresponding to a heart rate of the subject based on the heartbeat signal, and estimate a fundamental frequency of pulse rate of the subject by comparing the fundamental frequency of heart rate with the first photoplethysmogram signal and obtaining peak frequency components of the first photoplethysmogram signal that are closest to the fundamental frequency of the heart rate from among the frequency components of the first photoplethysmogram signal; and an information providing unit configured to provide information acquired based on the fundamental frequency of pulse rate.

2. The monitoring device according to claim 1, wherein the heartbeat signal is based on an electrocardiogram signal acquired from the subject.

3. The monitoring device according to claim 2, wherein the processing unit calculates the fundamental frequency of heart rate based on the electrocardiogram signal including a predetermined number or more of valid RR intervals within a predetermined time.

4. The monitoring device according to claim 3, wherein the processing unit determines whether the RR interval is valid based on whether the RR interval is associated with an arrhythmia, whether the RR interval is included in a predetermined value range, and whether the RR interval has a fluctuation less than a predetermined value.

5. The monitoring device according to claim 1, further comprising:

a filter configured to allow a signal in a specific frequency band to pass, wherein the processing unit sets the frequency band so as to include the estimated fundamental frequency of pulse rate, and calculates a pulse rate of the subject based on the first photoplethysmogram signal that passes through the filter, and wherein the information providing unit provides the calculated pulse rate as the information.

6. The monitoring device according to claim 1, further comprising:

a filter configured to allow a signal in a specific frequency band to pass, wherein the receiving unit receives a second photoplethysmogram signal acquired by irradiating the body with a second light having a second wavelength, the second wavelength has a different absorbance by a blood light absorber in the subject from that of the first wavelength, wherein the processing unit sets the frequency band so as to include the estimated fundamental frequency of pulse rate, and calculates a concentration of the blood light absorber based on the first photoplethysmogram signal and the second photoplethysmogram signal that pass through the filter, and wherein the information providing unit provides the calculated concentration of the blood light absorber as the information.

7. The monitoring device according to claim 1, wherein the processing unit specifies a part of the first photoplethysmogram signal corresponding to a pulse of the subject based on the estimated fundamental frequency of pulse rate, and wherein the information providing unit provides, as the information, the first photoplethysmogram signal, to which an annotation indicating the part corresponding to the pulse is added, in a visible manner.

8. The monitoring device according to claim 1, wherein the processing unit determines whether a probe that acquires the first photoplethysmogram signal is properly attached to the subject by comparing a frequency corresponding to the heart rate and the frequency component of the first photoplethysmogram signal, and wherein the information providing unit provides a result of the determination as the information.

9. The monitoring device according to claim 1, wherein the first light is infrared light.

10. The monitoring device according to claim 1, wherein the peak frequency components of the first photoplethysmogram signal that are less than a predetermined value different than the fundamental frequency of the heart rate from among the frequency components of the first photoplethysmogram signal are obtained.

11. A physiological signal processing device, comprising:

a receiving unit configured to receive a first photoplethysmogram signal acquired by irradiating a body of a subject with a first light having a first wavelength, and a heartbeat signal corresponding to a heartbeat of the subject; and a processing unit configured to calculate a fundamental frequency of heart rate corresponding to a heart rate of the subject based on the heartbeat signal, and estimate a fundamental frequency of pulse rate of the subject by comparing the fundamental frequency of heart rate with the first photoplethysmogram signal and obtaining peak frequency components of the first photoplethysmogram signal that are closest to the fundamental frequency of the heart rate from among the frequency components of the first photoplethysmogram signal.

12. The physiological signal processing device according to claim 11, wherein the peak frequency components of the first photoplethysmogram signal that are less than a predetermined value different than the fundamental frequency of the heart rate from among the frequency components of the first photoplethysmogram signal are obtained.

13. A non-transitory computer-readable medium configured to store a computer program executable by a processing unit of a physiological signal processing device, the computer program causing the physiological signal processing device to implement functions of:

receiving a first photoplethysmogram signal acquired by irradiating a body of a subject with a first light having a first wavelength;

receiving a heartbeat signal corresponding to a heartbeat of the subject;

calculating a fundamental frequency of heart rate corresponding to a heart rate of the subject based on the heartbeat signal; and estimating a fundamental frequency of pulse rate of the subject by comparing the fundamental frequency of heart rate with the first photoplethysmogram signal and obtaining peak frequency components of the first photoplethysmogram signal that are closest to the fundamental frequency of the heart rate from among the frequency components of the first photoplethysmogram signal.

14. The non-transitory computer-readable medium according to claim 13, wherein the peak frequency components of the first photoplethysmogram signal that are less than a predetermined value different than the fundamental frequency of the heart rate from among the frequency components of the first photoplethysmogram signal are obtained.

* * * * *